United States Patent [19]

Minami et al.

[11] Patent Number: Plant 6,864

[45] Date of Patent: Jun. 20, 1989

[54] NECTARINE TREE, "KAM RED"

[76] Inventors: Steven G. Minami, 8790 S. Buttonwillow; Gary R. Kitahara, P.O. Box 107, both of, Reedley, Calif. 93654

[21] Appl. No.: 194,229

[22] Filed: May 16, 1988

[51] Int. Cl.[4] ..... A01H 5/00

[52] U.S. Cl. ..... Plt./41

[58] Field of Search ..... Plt./41

*Primary Examiner*—James R. Feyrer

*Attorney, Agent, or Firm*—Worrel & Worrel

[57] ABSTRACT

A new and distinct nectarine tree denominated varietally as "Kam Red" and generally resembling the Flamekist nectarine tree (unpatented) but bearing a freestone fruit which is mature for harvesting and shipment approximately five to six days earlier than that of the Flamekist nectarine tree in the San Joaquin Valley of Central California.

1 Drawing Sheet

BACKGROUND OF THE NEW VARIETY

The present invention relates to a new and distinct variety of nectarine tree, denominated varietally as "Kam Red", and which is generally similar in its overall physical appearance to the Red Jim variety of nectarine tree (U.S. Plant Pat. No. 4,518), and the Flamekist nectarine tree (Unpatented), of which it is a newly found bud sport, but from which it is distinguished as to novelty by bearing a more deeply colored fruit which ripens for harvesting approximately August 7 through August 14 at Reedley, Calif., the subject variety ripening for harvest approximately five to six days earlier than the Flamekist variety of nectarine tree and approximately ten to eighteen days earlier than the Red Jim nectarine tree at the same geographical location.

The Flamekist nectarine tree (unpatented), which was originated by the Crops Research Division; Agricultural Research Service of the U.S. Department of Agriculture, is well known as a moderately vigorous producer of large, ovate, firm fleshed and clingstone fruit which are ripe for harvesting in Reedley, Calif. during the third week of August. Furthermore, the Flamekist nectarine tree has long been known for its attractive skin coloration and excellent eating qualities.

It has long been recognized that it would be desirable to have a nectarine tree which somewhat resembled the Flamekist nectarine tree but which bears fruit that ripen for harvesting earlier in the season whereby the commercial demand for such a nectarine can be effectively satisfied over a greater period of time.

ORIGIN AND ASEXUAL REPRODUCTION OF THE NEW VARIETY

The new and distinct variety of nectarine tree hereof was a chance bud sport discovered by the inventors in 1984 within the cultivated area of the Minami Ranch which is located at 10310 South Buttonwillow in Reedley, Calif. The bud sport, which was discovered by the applicants in a planting of Flamekist nectarine trees, was noted at that time to have desirable characteristics. Bud wood from this sport was procured by the applicants and grafted into test trees located on the same ranch. This first asexual propagation, which took place in 1986, resulted in progeny being produced that were found to possess the same distinctive characteristics as the original bud sport.

SUMMARY OF THE NEW VARIETY

The Kam Red variety of nectarine tree is characterized by many of the desirable characteristics of the Flamekist variety of nectarine tree (unpatented) but has the important distinction of bearing fruit that is more deeply colored than that of the Flamekist variety and which is ripe for harvesting and shipment approximately August 7 through August 14; this date of harvesting being approximately five to six days earlier than the Flamekist nectarine tree at the same geographical location. Further the fruit of the subject invention is freestone, in contrast to its parent, which is clingstone. Moreover, the fruit produced by the variety "Kam Red" possesses a flesh which is lightly yellow colored with some red coloration in the vicinity of the pit cavity at picking time.

BRIEF DESCRIPTION OF THE DRAWING

The accompanying drawing is a color photograph of five mature fruit of the subject variety, one of which has been divided in the suture plane to illustrate the flesh and pit characteristics; together with a twig bearing representative leaves which display the dorsal and ventral coloration thereof.

DETAILED DESCRIPTION

Referring more specifically to the pomological details of this new and distinct variety of nectarine tree, the following has been observed under the ecological conditions prevailing at the Minami Ranch which is located at 10310 South Buttonwillow in Reedley, Calif. All major color code plate identifications are by reference to the Dictionary of Color, by Maerz and Paul Second Edition. However, common color names are also employed occasionally.

TREE

Size:

*Generally.*—Average.

Figure: Spreading, open, and vase formed, depending upon pruning practices.

Vigor: Vigorous and hardy.

Productivity: Productive.

Regularity of bearing: Regular.

Trunk:

*Size.*—Medium.

*Texture.*—Average nectarine type bark.

Branches:

*Size.*—Generally — average.

*Texture.*—Average nectarine type bark.

*Color — gray.*—The color of the branches is not particularly distinctive.

*Color — immature growth.*—A dull green. This color is not particularly distinctive of the instant variety.

Leaves:

*Size.*—Generally — Average.

*Length.*—Approximately 90–100 mm.

*Width.*—Approximately 28–30 mm.

*Shape.*—Lanceolate.

*Thickness.*—Average.

*Color — upper surface.*—Plate 23, L-12 (page 69).

*Color — lower surface.*—Plate 23, L-3 (page 69).

Marginal form: Finely serrate.

Glandular characteristics:

*Numbers.*—Variable — two or three glands may be found.

*Position.*—Opposite.

*Size.*—Average.

*Form.*—Reniform.

*Color.*—Green; this color is not particularly distinctive of the instant variety.

*Stipules.*—Not present.

Petiole:

*Length.*—Average, approximately 12 mm.

*Thickness.*—Medium — approximately 2 mm.

Flower Buds:

*Size.*—Average, approximately 7 to 8 mm.

*Form.*—Plump and generally obtuse.

*Surface texture.*—Pubescent.

Flowers:

*Date of bloom.*—In 1988 the first bloom occurred on Feb. 22, 1988, full bloom was achieved on Mar. 1, 1988, and petal fall was observed on Mar. 7, 1988.

*Size.*—Variable, medium to large, approximately 25 mm.

*Petal color — upper side.*—Pink, Plate 49, E-4 (page 121).

*Petal color — lower side.*—Pink, Plate 49, G-5 (page 121).

Pistil:

*Numbers.*—One.

Stamens:

*Numbers.*—Variable, 50 or 51.

FRUIT

Maturity when described: Hard ripe. The subject variety is ripe for harvesting and shipment August 7 through August 14 in Reedley, Calif.

*Size.*—Generally — average.

*Uniformity.*—Uniform.

*Axial diameter.*—Approximately 66 through 69 mm.

*Diameter transverse in the suture plane.*—Approximately 63 through 69 mm.

*Diameter at right angles to the suture plane.*—Approximately 64 through 70 mm.

Form:

*Uniformity.*—Uniform.

*Symmetry.*—Round, with unequal sides.

Suture: The suture of the subject variety appears as a distinct but shallow line which extends from the base to the apex. The suture appears over the entire circumference. A slight depression is evident beyond the pistil point.

Ventral surface: Rounded slightly.

Stem cavity:

*Generally.*—Abrupt, and elongated in the suture plane with the suture appearing on one side.

*Depth.*—Approximately 10 to 14 mm.

*Breadth.*—Approximately 11 to 16 mm.

*Length in the suture plane.*—Approximately 20 to 26 mm.

Base:

*Shape.*—Rounded.

Apex:

*Shape.*—Short and depressed.

Pistil point:

*Position.*—Oblique.

Skin:

*Generally.*—Average.

*Thickness.*—Medium.

*Tendency to crack.*—Slight.

*Blush color.*—Red, Plate 7, L-3 (page 37).

*Ground color.*—Yellow, Plate 9, L-12 (page 41).

Flesh:

*Color.*—The flesh is colored yellow next to the skin and mottled with red next to the stone and pit cavity.

*Flesh color near the skin.*—Yellow, Plate 9, L-12 (page 41).

*Flesh color near the pit.*—Red, Plate 7, L-5 (page 37).

*Amygdalin.*—Scant.

*Flesh texture.*—Average.

*Fibers.*—Few, fine and tender.

*Ripening.*—Even.

Flavor: Subacid.

Eating quality: Good.

Stone:

*Generally.*—Freestone.

*Fibers.*—Length — Short.

*Size.*—Generally — Average.

*Length.*—Approximately 34 to 36 mm.

*Breadth.*—Approximately 25 to 26 mm.

*Thickness.*—Approximately 19 to 20 mm.

*Form.*—Generally — Oblong.

*Base.*—Straight.

*Sides.*—Equal.

*Apex.*—Rounded and acute.

*Surface texture.*—Irregularly furrowed near the base.

*Ridges.*—Generally — jagged.

*Ventral edge.*—Thin.

*Dorsal edge.*—Narrow.

*Color of stone.*—Red, Plate 7, L-5 (Page 37).

*Tendency to split.*—Slight.

Use: Dessert.

Keeping quality: Good.

Resistance to disease and insects: Good. No particular susceptibilities were noted.

Shipping quality: Above average.

Although the new variety of nectarine tree possesses the desirable characteristics noted under the growing conditions prevailing in Reedley, Calif., in the central part of the San Joaquin Valley, it is to be understood that variations of the usual magnitude and characteristics incident to changes in growing conditions, fertilization, pruning and pest control are to be expected.

Having thus described and illustrated our new variety of nectarine tree, what we claim as new and desire to secure by Plant Letters Patent is:

1. A new and distinct variety of nectarine tree substantially as illustrated and described which is characterized as to novelty by bearing a freestone fruit having a firm flesh and by its general resemblance to the Flamekist nectarine tree (unpatented) from which it was derived as a bud sport but from which it is distinguished therefrom by its bearing fruit which matures for harvesting approximately August 7 through August 14, this date of maturity being approximately five to six days earlier than that of the Flamekist nectarine tree and by producing fruit which have a skin which is more deeply colored than that exhibited by the fruit of the Flamekist nectarine tree.

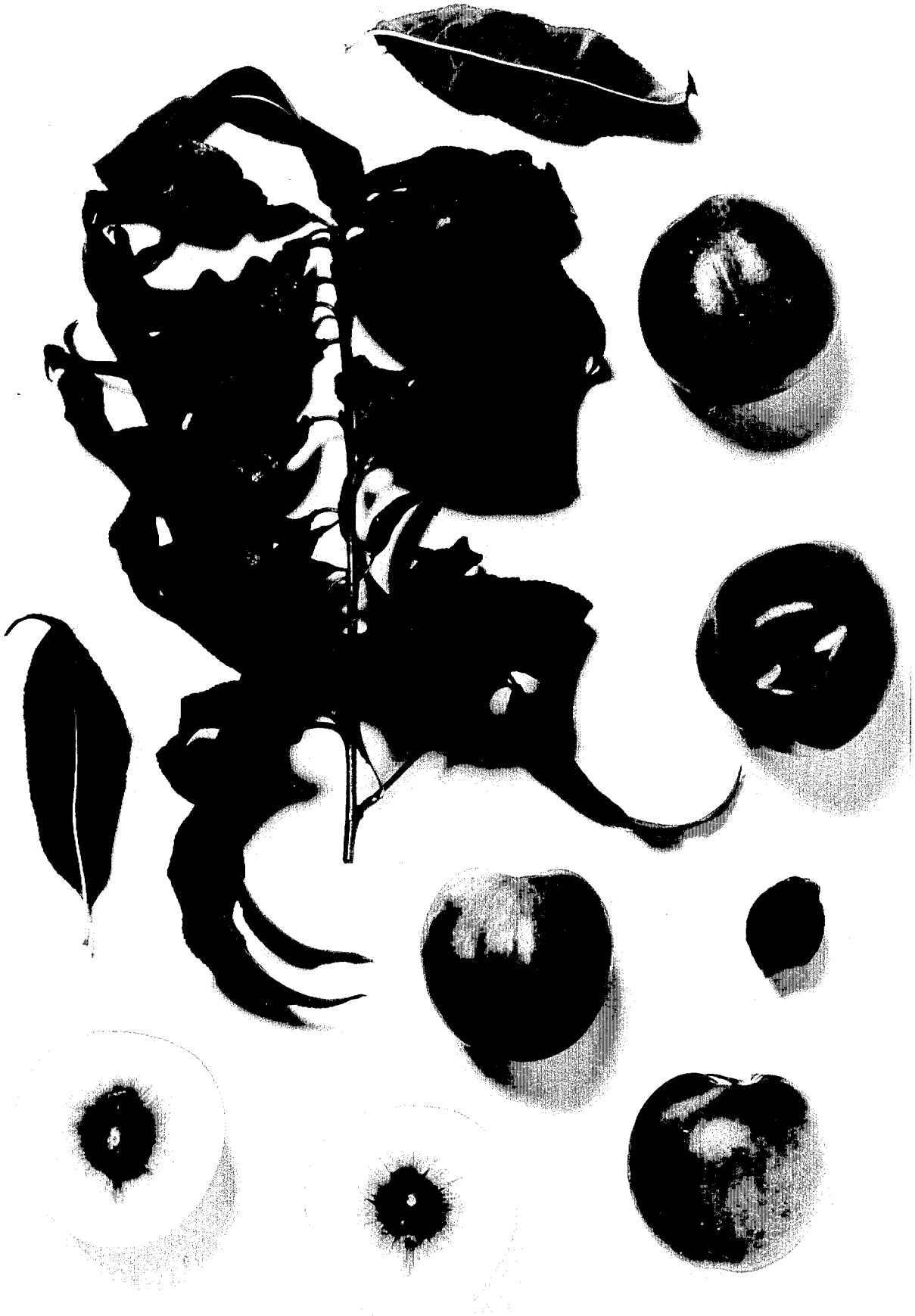

* * * * *